United States Patent
Wang et al.

(10) Patent No.: US 9,952,196 B2
(45) Date of Patent: Apr. 24, 2018

(54) METHOD FOR DETECTING ALBUMIN BASED ON COLORIMETRIC ASSAY AND SYSTEM THEREOF

(71) Applicant: NATIONAL CHUNG CHENG UNIVERSITY, Min-Hsiung, Chia-Yi (TW)

(72) Inventors: Shau-Chun Wang, Chiayi (TW); Teh-Sheng Lai, Tainan (TW); Ting-Chou Chang, Dounan Township, Yunlin County (TW)

(73) Assignee: National Chung Cheng University, Chia-Yi (TW)

( * ) Notice: Subject to any disclaimer, the term of this patent is extended or adjusted under 35 U.S.C. 154(b) by 342 days.

(21) Appl. No.: 14/985,986

(22) Filed: Dec. 31, 2015

(65) Prior Publication Data
US 2017/0146507 A1 May 25, 2017

(30) Foreign Application Priority Data
Nov. 23, 2015 (TW) .............................. 104138852 A

(51) Int. Cl.
*G01N 33/487* (2006.01)
*B01D 61/44* (2006.01)
(Continued)

(52) U.S. Cl.
CPC ........... *G01N 33/487* (2013.01); *B01D 61/44* (2013.01); *B01D 61/46* (2013.01); *B01L 3/50* (2013.01);
(Continued)

(58) Field of Classification Search
CPC ............. G01N 33/487; G01N 33/6827; G01N 21/554; G01N 1/4005; G01N 27/44791; G01N 21/251; G01N 27/44721; G01N 2001/4011; G01N 2201/0221; G01N 2201/12; G01N 2333/76; B01D 61/44; B01D 61/46; B01D 2311/02; B01D 2311/2623; B01D 2311/2684; B01L 3/50
See application file for complete search history.

(56) References Cited

PUBLICATIONS

Chen et al., "Selective dynamic concentration of peptides at poles of cation-selective nanoporous granules" Biomicrofluidics, (Jul. 2013). vol. 7, pp. 044110-1-044110-9.
(Continued)

*Primary Examiner* — Dennis White
(74) *Attorney, Agent, or Firm* — Muncy, Geissler, Olds & Lowe, P.C.

(57) ABSTRACT

A method for detecting albumin based on a colorimetric assay and a system thereof are disclosed. Gold nanoparticles are added into the sample preparing device having a sample without spectroscopic tags, wherein the sample without spectroscopic tags is formed as the alkaline solution to avoid the interference substances adhering on the gold nanoparticles. The gold nanoparticles are concentrated by using the microfluidic concentrator with the circular ion exchange membrane by applying an external electric field across two electrodes. The image of the concentrated gold nanoparticles is captured by the image capturing device for measuring the saturation intensities of the image, wherein there is a relation between the saturation intensities and the concentration of the albumin in the sample without spectroscopic tags. The concentration of the albumin of the sample without spectroscopic tags is obtained by the relation and the measured saturation intensities.

10 Claims, 3 Drawing Sheets

(51) Int. Cl.
*B01D 61/46* (2006.01)
*G01N 21/25* (2006.01)
*G01N 27/447* (2006.01)
*B01L 3/00* (2006.01)
*G01N 1/40* (2006.01)
*G01N 21/552* (2014.01)
*G01N 33/68* (2006.01)

(52) U.S. Cl.
CPC ......... *G01N 1/4005* (2013.01); *G01N 21/251* (2013.01); *G01N 21/554* (2013.01); *G01N 27/44721* (2013.01); *G01N 27/44791* (2013.01); *G01N 33/6827* (2013.01); B01D 2311/02 (2013.01); B01D 2311/2623 (2013.01); B01D 2311/2684 (2013.01); G01N 2001/4011 (2013.01); G01N 2201/0221 (2013.01); G01N 2201/12 (2013.01); G01N 2333/76 (2013.01)

(56) References Cited

PUBLICATIONS

Wang et al., "Dynamic Super-Concentration at Critical-Point Double-Layer Gates of Nanoporous Conducting Granules" Biomicrofluidics 2008, vol. 2, pp. 014102-1-014102-9.

METHOD FOR DETECTING ALBUMIN BASED ON COLORIMETRIC ASSAY AND SYSTEM THEREOF

CROSS-REFERENCE TO RELATED APPLICATION

This application claims priority from Taiwan Patent Application No. 104138852, filed on Nov. 23, 2015, in the Taiwan Intellectual Property Office, the content of which is hereby incorporated by reference in their entirety for all purposes.

BACKGROUND OF THE INVENTION

1. Field of the Invention

This application relates to a method for detecting albumin and a system thereof, and more particularly, to a method for detecting albumin based on the colorimetric assay and a system thereof.

2. Description of the Related Art

Recently, the method for detecting gold nanoparticle aggregation based on the colorimetric assay has become a bio analyzing and sensing method. When the colloidal gold nanoparticles are dispersed or aggregated forms, it may possess a strong extinction coefficient for facilitating observation. On account of the transformation of the property of particle plasmon resonance, when nanoparticles are aggregated, the color of the solution containing the gold nanoparticles may change from red into blue. The aggregation may be triggered by the variations of the content of the solution so as to combining tiny nanoparticles through chemical bond or hydrogen bond.

In order to determine the albumin, the conventional method is to dock the functionalized gold nanoparticles having molecular probes to the target albumin to form the aggregation to result in the color change. Recently, the detection of albumin and lysozyme based on the colorimetric assay has also been published using the hydrophobicity of gold nanoparticles to absorb proteins. As a result, the blue aggregation can be avoided due to the electrical charge repulsion of absorbed proteins.

Therefore, the nanochannel containing the surface charge may be served as the ion selection device. It is because when the co-ion is repelled by the electrostatic repulsion of the surface charge, only the counter ion with opposite electrical polarity can stay in the electrical double layer (EDL). When applying an external electric field across two electrodes, the counter ions in a steady state maintain in a continuous flow, but the co-ion flow may stop in the contact of the nanochannel. Consequently, a great deal of ions being polarized may happen at two sides of the nano porous substrate. As far as the cation exchange substrate is concerned, when the ion is accumulated at side of cathode to satisfy with the mass conversation and electrical neutrality, the ion depletion region appears at side of anode.

When the ion exchange membrane substrate is circular, it may converge the electric field lines from one side to the other side of the surface according to the aforementioned filtering dynamics. Afterwards, when the surface electroosmotic flows transport the counter ions near the membrane, these ions are further driven by the funnel-shaped converging field lines through the membrane to concentrate toward the other side. When the concentrated ions are injected to the bulk region with electrical neutrality, they attract the co-ions and result in the concentration too. Hence, the converged field lines passing through the circular substrate particles may focus in the exit to enhance the condensation polarization. So, the aforementioned ion concentration aggregation mechanism is used to the microfluidic concentrator for improving the detection sensitivity. As a result, applying the microfluidic concentrator is able to greatly improve the detection sensitivity of the albumin of fluorescent tags and peptide. [Reference: (1) Hsiao-Ping Chen, Chia-Chun Tsai, Hung-Meng Lee, Shau-Chun Wang, Hsueh-Chia Chang (2013, Jul). "Selective dynamic concentration of peptides at poles of cation-selective nanoporous granules" Biomicrofluidics, 7, 044110; (2) Wang, S.-C.; Wei, H.-H.; Chen, H.-P.; Tsai, M.-H; Yu, C.-C.; Chang, H.-C. "Dynamic Super-Concentration at Critical-Point Double-Layer Gates of Nanoporous Conducting Granules" Biomicrofluidics 2008, 2, 014102]

In addition, analyzing the total albumin content is the most popular method for screening the patients who suffer from the proteinuria. Here, the application of the semiquantitative determination is convenient but is not of precision. Applying the dye-staining method may be able to achieve the quantitative determination precisely to avoid the test error though; it has to be performed in the lab and cannot be done in field settings. Hence, developing a portable apparatus which is capable of precisely testing the concentration of albumin in the field is still needed.

SUMMARY OF THE INVENTION

In view of the foregoing technical problems, the objective of the present provides a method for detecting albumin based on the colorimetric assay and a system thereof to quantitatively analyze the concentration of the albumin in clinical samples, such as urine. Here, the system of the present disclosure is integrated into a mobile communication device disposed with a photographing device to observe the variations of colors when concentrating the gold nanoparticles in different albumin levels in the observation accommodating reservoir. The saturation intensities of the image can be decoded to calculate the color intensity. As a consequence, the present disclosure applies the relation such as a linear relation between the saturation intensities (not adding extra fluorescent tags) and a concentration of albumin to detect the concentration of albumin, such that adding extra fluorescent tags into the present disclosure is unnecessary. In addition, the present disclosure only applies the conventional image capturing device disposed with the image sensor such as a phone or mobile device and so on to perform the aforementioned processes without using extra apparatuses such as a fluorescent microscope, a mercury lamp, and so on.

In view of the foregoing technical problems, the objective of the present provides a method for detecting albumin based on the colorimetric assay, including the following steps of: adding gold nanoparticles into a sample preparing device having a sample without spectroscopic tags, preparing the sample without spectroscopic tags to form an alkaline solution to avoid interference substances adhering on the gold nanoparticles; concentrating the gold nanoparticles by using a microfluidic concentrator with a circular ion exchange membrane and by applying an external electric field across two electrodes; capturing an image of the concentrated gold nanoparticles by an image capturing device for measuring saturation intensities of the image, wherein there is a relation between the saturation intensities and a concentration of the albumin in the sample without spectroscopic tags; and obtaining the concentration of the albumin of the sample without spectroscopic tags by using the relation and the measured saturation intensities.

Preferably, the saturation intensities include a saturation intensity difference among three primary colors of the image.

Preferably, the relation denotes a linear relation between the saturation intensity difference and a logarithm of the concentration of the albumin.

Preferably, a pH value of the alkaline solution is substantially 10.

Preferably, the image capturing device is a charge coupled device or a complementary metal oxide semiconductor image sensor built in a mobile device.

In addition, the present disclosure further provides a system of detecting albumin based on the colorimetric assay, including: a sample preparing device having a sample without spectroscopic tags, gold nanoparticles added into the sample preparing device, wherein the sample without spectroscopic tags are prepared to form an alkaline solution to avoid interference substances adhering on the gold nanoparticles when the gold nanoparticles are added into the sample preparing device having the sample without spectroscopic tags; a microfluidic concentrator concentrating the gold nanoparticles by using a circular ion exchange membrane and by applying an external electric field across two electrodes; an image capturing device capturing an image of the concentrated gold nanoparticles for measuring saturation intensities of the image, wherein there is a relation between the saturation intensities and a concentration of the albumin in the sample without spectroscopic tags; and a processing device, the image capturing device transmitting the saturation intensities to the processing device, and the processing device obtaining the concentration of the albumin of the sample without spectroscopic tags by using the relation and the measured saturation intensities.

Preferably, the system of detecting albumin based on the colorimetric assay further includes a storage storing the relation.

Preferably, the saturation intensities include a saturation intensity difference among three primary colors of the image, and the relation denotes a linear relation between the saturation intensity difference and a logarithm of the concentration of the albumin.

Preferably, a pH value of the alkaline solution is substantially 10.

Preferably, the image capturing device is a charge coupled device or a complementary metal oxide semiconductor image sensor built in a mobile device.

As a consequence, a method for detecting albumin based on the colorimetric assay and a system thereof of the present disclosure may have one or more advantages as follows.

1. By adding gold nanoparticles into a sample preparing device having a sample without spectroscopic tags and then concentrating the added gold nanoparticles, a relation such as a linear relation between the saturation intensities (not adding extra fluorescent tags) and a concentration of albumin is applied to detect the concentration of albumin, such that adding extra fluorescent tags into the present disclosure is unnecessary. In addition, the present disclosure only applies the conventional image capturing device disposed with the image sensor such as a phone or mobile device and so on to perform the aforementioned processes without using extra apparatuses such as a fluorescent microscope, a mercury lamp, and so on.

2. By preparing the sample without spectroscopic tags to form an alkaline solution is able to avoid interference substances adhering on the gold nanoparticles 3. By replacing the particles of the conventional ion-exchange resin with a circular ion exchange membrane can have the same effect for contributing to the observation.

DETAILED DESCRIPTION OF THE PREFERRED EMBODIMENTS

Hereinafter, embodiments of the present invention will be described in detail with reference to the accompanying drawings so that those skilled in the art to which the present invention pertains can realize the present invention. As those skilled in the art would realize, the described embodiments may be modified in various different ways, all without departing from the spirit or scope of the present invention.

Figure 1:
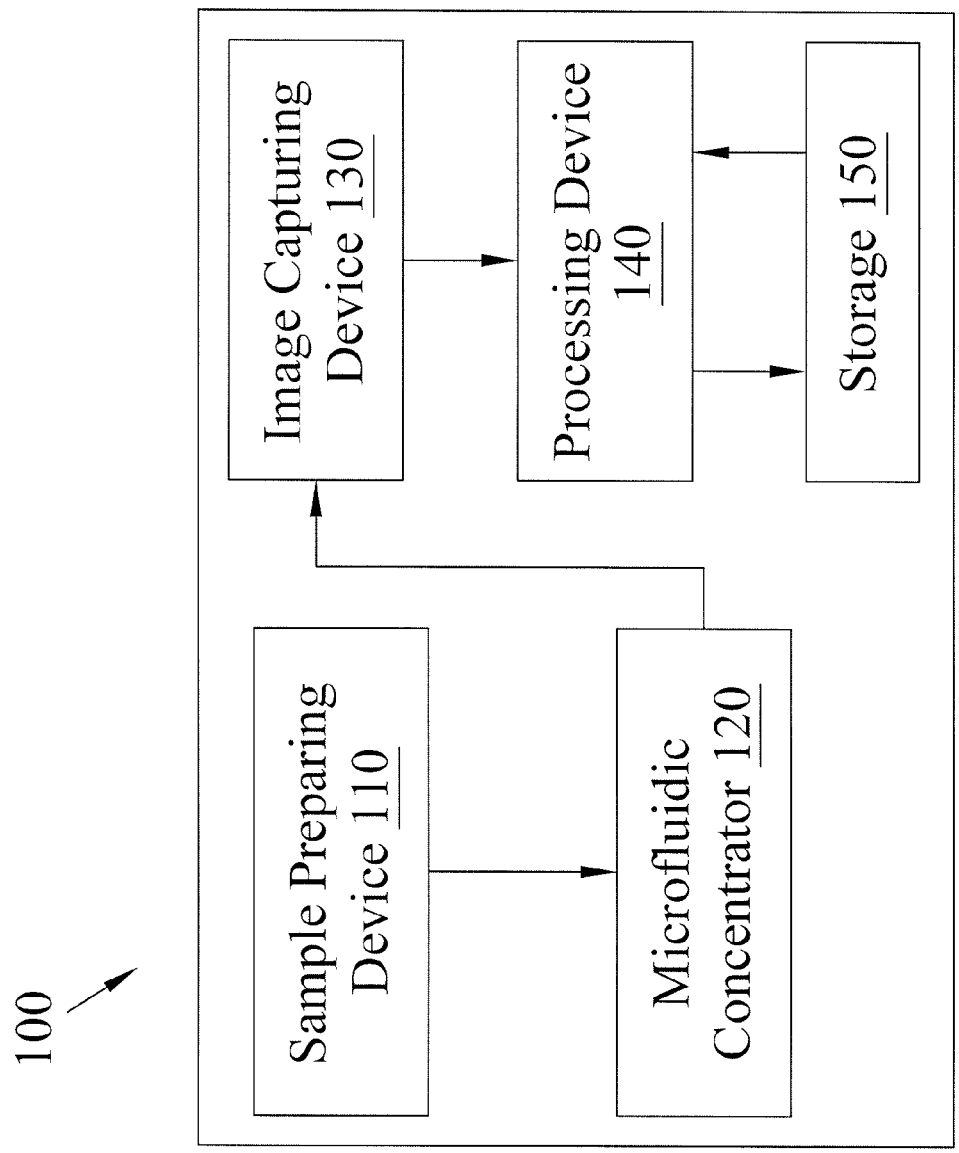
FIG. 1 is a block diagram of a system of detecting albumin based on the colorimetric assay according to the present disclosure.
Figure 2:
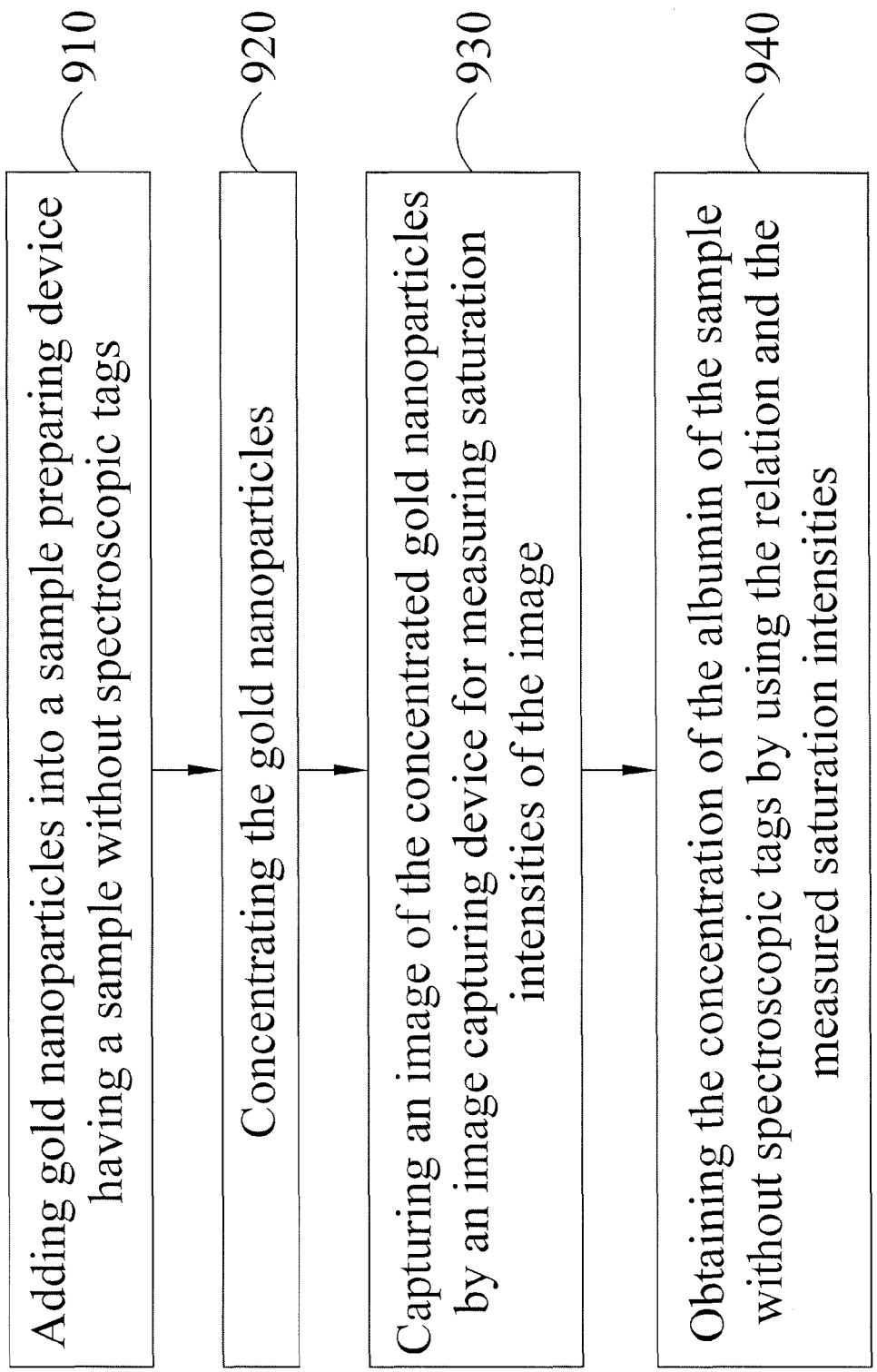
FIG. 2 is a flow chart of a method for detecting albumin based on the colorimetric assay according to the present disclosure.
Figure 3:
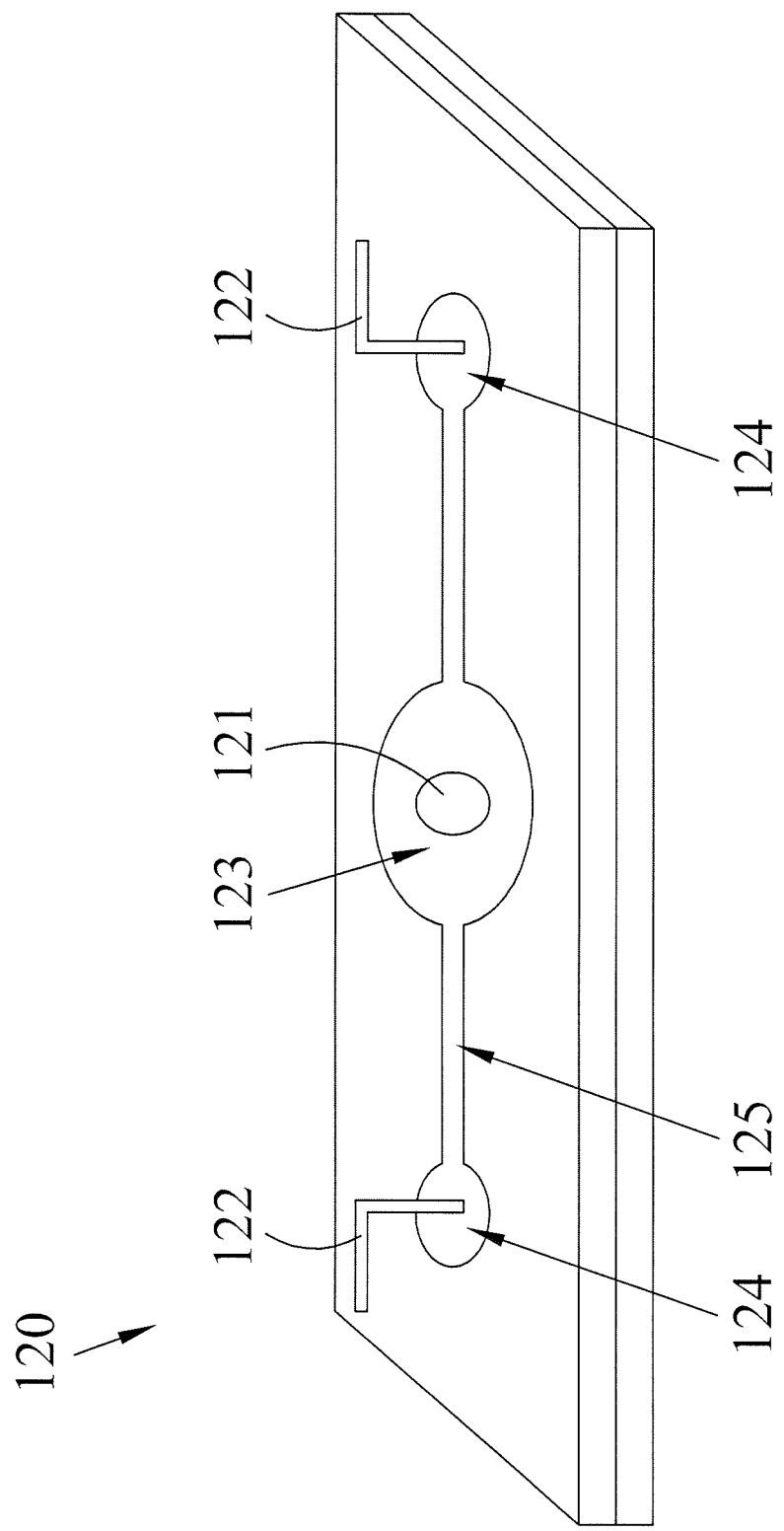
FIG. 3 is a schematic diagram illustrating structure for a microchannel concentrating apparatus of the present disclosure.

Please refer to FIG. 1 to FIG. 3, which are a block diagram of a system of detecting albumin based on the colorimetric assay according to the present disclosure, a flow chart of a method for detecting albumin based on the colorimetric assay according to the present disclosure, and a schematic diagram illustrating structure for a microchannel concentrating apparatus of the present disclosure, respectively. As shown in the figures, a method for detecting albumin based on the colorimetric assay according to the present disclosure includes the following of: adding gold nanoparticles into a sample preparing device having a sample without spectroscopic tags and preparing the sample without spectroscopic tags to form an alkaline solution to avoid interference substances adhering on the gold nanoparticles (step 910); concentrating the gold nanoparticles by using a microfluidic concentrator with a circular ion exchange membrane and by applying an external electric field across two electrodes (step 920); capturing an image of the concentrated gold nanoparticles by an image capturing device for measuring saturation intensities of the image, wherein there is a relation between the saturation intensities and a concentration of the albumin in the sample without spectroscopic tags (step 930); and obtaining the concentration of the albumin of the sample without spectroscopic tags by using the relation and the measured saturation intensities of the image captured by the image capturing device (step 940).

Here, there are a plurality of gold nanoparticles, and the sample has no any spectroscopic tags such as fluorescent materials or marked substances or materials coated therein. Hereby, the method for detecting albumin based on the colorimetric assay according to the present disclosure detects the albumin based on the colorimetric assay when the gold nanoparticles aggregate without extra apparatuses such as a fluorescent microscope, a mercury lamp, and so on.

Here, the sample without spectroscopic tags has the albumin which is pending to be detected. For the sake of avoiding interference substances adhering on the gold nanoparticles to affect the detection precision, before the gold nanoparticles is added into the sample preparing device 110 having the sample without spectroscopic tags, the method for detecting albumin based on the colorimetric assay according to the present disclosure is to prepare the sample without spectroscopic tags to form an alkaline solution to avoid interference substances adhering on the gold nanoparticles. And a pH value of the alkaline solution is substantially 10.

The microfluidic concentrator 120 applied in step 920 is consisted of two thermoplastic slides, and has a size of 7.5 cm of length, 2.5 cm of width and 0.1 com of thickness. But the present disclosure shall be not limited thereto. Contrarily, the microfluidic concentrator 120 is feasible to utilize any materials and sizes. In addition, the microfluidic concentrator 120 includes a central accommodating reservoir 123 and recesses 124 disposed at two sides of the central accommodating reservoir 123. The recesses 124 and the central accommodating reservoir 123 are communicated with each other through a microfluidic channel 125. Here, top views of the recesses 124 and the central accommodating reservoir 123 may be circle. The central accommodating reservoir 123 has a diameter of 0.6 cm. The recesses 124 have a diameter of 0.3 cm. Moreover, the central accommodating reservoir 123 is disposed with a circular ion exchange membrane to perform the concentration. The recesses 124 are respectively disposed with two platinum electrodes 122. The two platinum electrodes 122 are connected to a power source supplied by an external power supply apparatus (not shown in figures), so that the microfluidic concentrator 120 generate ion current.

The circular ion exchange membrane applied in the present disclosure is formed according to the following steps. Firstly, a carbon dioxide laser system is applied to burn a PDMS mold having about 0.5 mm thickness to form circular orifices with a diameter of 3 mm. Next, a specific solution is added into each circular orifice to form a cation exchange membrane substrate. The mold is heated over 10 minutes at a temperature of about 120 degrees so as to increase the mechanical strength of the cation exchange membrane substrate. Afterwards, the cation exchange membrane substrate is removed from the mold and then washed by ion water by about three minutes. Accordingly, the cation exchange membrane substrate is swelling in a strong acid of 1M and sodium hydroxide of 1M. As a consequence, it can obtain the circular ion exchange membrane 121 disposed on the microfluidic concentrator 120 of the present disclosure. However, it is noteworthy that the circular ion exchange membrane 121 shall be not limited to the manufacturing mentioned above.

In step 920, the sample preparing device 110 having the sample without spectroscopic tags mixed with the gold nanoparticles is filled in the space of the microfluidic concentrator 120 formed by the central accommodating reservoir 123, the recesses 124, and the microfluidic channel 125. The external power supply apparatus applies an external electric field across the two platinum electrodes 122 disposed in the recesses 124 by about 100 volt/cm, such that the sample preparing device 110 having the sample without spectroscopic tags mixed with the gold nanoparticles filled in the microfluidic concentrator 120 generates an ion current. When the ion current passes through the circular ion exchange membrane 121 in the central accommodating reservoir 123, the gold nanoparticles are concentrated in the sample preparing device 110 on account of the ion-exchange property. Here, the microfluidic concentrator 120 having the circular ion exchange membrane 121 has an effect of concentration by 10,000 times. In addition, the circular ion exchange membrane (not the particles of the conventional ion-exchange resin) applied in the present disclosure is capable of showing the same effect for contributing to the observation.

Here, the dispersed gold nanoparticles are red. When being concentrated, the dispersed gold nanoparticles concentrate to form a cluster which is blue or blue violet. When the gold nanoparticles are added into the sample without spectroscopic tags, the albumin in the sample without spectroscopic tags contacts the gold nanoparticles and accordingly coat on the gold nanoparticles. When sample without spectroscopic tags is formed as an alkaline solution, the albumin dissociates to generate negative charge. Hence, when the albumin has a higher concentration, the gold nanoparticles cannot produce a cluster easily because of the electrical repulsion forces between the negatively charged albumin-coated nanoparticles. That is to say, when the concentration of albumin is higher, the microfluidic concentrator 120 concentrates the gold nanoparticles through the circular ion exchange membrane 121 and the electrical field across the two electrodes 122. Afterwards, the gold nanoparticles of the sample preparing device 110 are red. When the albumin in the sample without spectroscopic tags has a lower concentration, an amount of albumin becomes less as the effect of electrical repulsion. Hence, when the microfluidic concentrator 120 concentrates the gold nanoparticles using the circular ion exchange membrane 121 and the electrical field across the two electrodes 122, the gold nanoparticles of the sample preparing device 110 aggregate and are blue or blue violet. That is, after performing step 920, the gold nanoparticles concentrated by the method for detecting albumin based on the colorimetric assay of the present disclosure has a relation between saturation intensities and a concentration of the albumin in the sample without spectroscopic tags. Furthermore, a linear relation between the saturation intensity difference and a logarithm of the concentration of the albumin may appear.

As a result, in step 930, the method for detecting albumin based on the colorimetric assay of the present disclosure only needs an image capturing device 130 to capture an image of the concentrated gold nanoparticles, it can obtain the saturation intensities of the image. A processing device 140 applies the measured saturation intensities of the image and the relation to determine the concentration of the albumin in the sample without spectroscopic tags. Here, the image capturing device 130 may be a charge coupled device (CCD) or a complementary metal oxide semiconductor (CMOS) image sensor built in a mobile device. The saturation intensities include a saturation intensity difference among three primary colors of the image. In addition, the relation denotes a linear relation between the saturation intensity difference and a logarithm of the concentration of the albumin. Moreover, the processing device 140 may be a computer or the other calculation apparatuses. The image capturing device 130 may directly or indirectly transmits the saturation intensities to the processing device 140 through internet, transmission line or any other physical devices, but it shall be not limited thereto. The processing device 140 may be a processor built-in a mobile device. The processing device 140 and the image capturing device 130 may be built-in the same or different mobile devices.

For example, when the user utilizes a mobile device disposed with the image capturing device 130 and a basic calculation device, an application (APP) containing the concept with respect to the present disclosure may be downloaded in advance, such that the basic calculation device of the mobile device may be the processing device 140 applied in the present disclosure. Alternatively, the user may apply the mobile device disposed with the image capturing device 130 to capture the image, and then directly or indirectly transmits the saturation intensities of the image to the processing device 140 such as a computer or any other calculation apparatuses through internet, transmission line or any other physical devices. That is to say, in step 930, the user only utilizes the image capturing device 130 of the mobile device or any external image capturing device 130 to capture the image of the concentrated gold nanoparticles in the microfluidic concentrator 120. Afterwards, the image capturing device 130 transmits the image to the processing 140, such that the processing device 140 receives the image and the saturation intensities of the image. The saturation intensities among three primary colors of the image, namely, the saturation intensities of red, green and blue, are applied to be calculated so as to obtain a saturation intensity difference among three primary colors of the image. Here, the processing device 140 may have a calculation according to Formula (1) to obtain the saturation intensity difference among three primary colors of the image, but it shall be not limited thereto.

$$I=[(L_{red}-L_{blue})+(L_{red}-L_{green})]/2 \quad (1)$$

Besides, the image capturing device 130 captures the images of the gold nanoparticles in the microfluidic concentrator 120 and the images of the gold nanoparticles in the central accommodating reservoir 123 or only captures the mature image of partial gold nanoparticles so as to hereby obtain the saturation intensities with respect to the albumin according to actual requirements. Furthermore, before step 940, the method for detecting albumin based on the colorimetric assay of the present disclosure stores a relation between the saturation intensities and the concentration of albumin in a storage 150 in advance, so that when the processing device 140 obtains the saturation intensities, the storage 150 is controlled to transmit the relation to the processing device 140 so as to calculate the concentration of the albumin in the sample without spectroscopic tags according to the measured saturation intensities and the received relation. Here, the storage 150 may be built in the mobile device and is electrically connected to the processing device 140 and even to the image capturing device 130, such that the storage 150 stores the relation, it can further stores the image captured by the image capturing device 130 and/or the saturation intensities obtained by the processing device 140 and the concentration of albumin in the sample without spectroscopic tags. However, the present invention shall be not limited thereto. On the contrary, the present disclosure bay transmit message to an external storage such as cloud database to require the relation between the saturation intensities and the concentration of albumin before or when the processing device 140 obtains the saturation intensities of the image. That is to say, the storage 150 may be a storage element disposed in the processing device 140, mobile storage device or external storages such as cloud database, cloud hard drive, and so on.

Here, the storage 150 stores the relation between the saturation intensities and the concentration of the albumin in the sample without spectroscopic tags or a membership function, such that when the processing device 140 obtains the saturation intensities in step 940, it can obtain the concentration of albumin corresponding to the saturation intensities by looking table or through the calculation of the function. For example, if the processing device 140 obtains the saturation intensities according the aforementioned Formula (1), a linear relation between the saturation intensity difference and a logarithm of the concentration of the albumin may appear to. Consequently, the storage 150 only stores the function concerning the linear relation, so that when the processing device 140 obtains the saturation intensities or after the processing device 140 obtains the saturation intensities, the function received from the storage 150 and the measured saturation intensities and the function of the linear relation are applied to the calculate the concentration of albumin in the sample without spectroscopic tags.

That is to say, adding gold nanoparticles into a sample preparing device having a sample without spectroscopic tags such as fluorescent tags is unnecessary to the method for detecting albumin based on the colorimetric assay of the present disclosure. Hence, the present disclosure only applies the image capturing device disposed with the image sensor such as a cell or a mobile device without adding the external apparatuses such as a fluorescent microscope, a mercury lamp, and so on. In addition, by means of preparing the sample without spectroscopic tags to form an alkaline solution, the present disclosure is able to avoid interference substances adhering on the gold nanoparticles so as to prevent the decrease of the detection sensitivity. Moreover, the circular ion exchange membrane applied in the present disclosure is capable of showing the same effect for contributing to the observation.

Although the method for detecting albumin based on the colorimetric assay of the present disclosure has been detailed as above, the following paragraphs will describe for more details. Here, a system of detecting albumin based on the colorimetric assay of the present disclosure can be referred to aforementioned description.

As shown in FIG. 1, the system 100 of detecting albumin based on the colorimetric assay of the present disclosure includes a sample preparing device 110 having a sample without spectroscopic tags, a microfluidic concentrator 120 having a circular ion exchange membrane, an image capturing device 130 and a processing device 140. In addition, the image capturing device 130, the processing device 140 and the storage 150 are integrated into a mobile device. Alternatively, the image capturing device 130, the processing device 140 and the storage 150 may be an image capturing module, a central processor and a storage module built-in a mobile device. The mobile device may be a smartphone, tablet or any mobile devices with photographing function. In addition, the processing device 140 may be an independent device outside the mobile device, and the storage 150 may be an independent device outside the mobile device. That is, the processing device 140 may be a computer or any calculation apparatuses, and the storage 150 may be the storage element disposed in the processing device 140, extra mobile storages such as cloud database or external storage devices such as cloud hard drive, and so on.

Here, gold nanoparticles are added into a sample preparing device 110 having a sample without spectroscopic tags. The sample without spectroscopic tags may be a solution containing albumin. When the gold nanoparticles are added into a sample preparing device 110 having the sample without spectroscopic tags or after the gold nanoparticles are added into a sample preparing device 110 having the sample without spectroscopic tags, the sample without spectroscopic tags is prepared to form an alkaline solution to avoid interference substances adhering on the gold nanoparticles. Here, a pH value of the alkaline solution is substantially 10. A microfluidic concentrator 120 concentrates the gold nanoparticles by using a circular ion exchange membrane 121 and by applying an external electric field across two electrodes. Here, the electrode may be a platinum electrode 122.

An image capturing device 130 captures an image of the concentrated gold nanoparticles for measuring saturation intensities of the image, wherein there is a relation between the saturation intensities and a concentration of the albumin in the sample without spectroscopic tags, and the saturation intensities include a saturation intensity difference among three primary colors of the image, and the relation denotes a linear relation between the saturation intensity difference and a logarithm of the concentration of the albumin. In addition, the image capturing device 120 is a charge coupled device (CCD) or a complementary metal oxide semiconductor image sensor (CMOS) built in a mobile device. Here, the relation between the saturation intensities and a concentration of the albumin in the sample without spectroscopic tags is stored in the storage 150, and the storage 150 is electrically connected to the processing device 140. The storage 150 directly or indirectly transmits the relation to the processing device 140 through the processing device 140 or other manners. Furthermore, the image capturing device 130 transmits the image and/or the saturation intensities to the processing device 140, such that the processing device 140 applies the measure saturation intensities and the relation obtained from the storage 150 to obtain the concentration of albumin in the sample without spectroscopic tags.

Hereby, adding gold nanoparticles into a sample preparing device having a sample without spectroscopic tags such as fluorescent tags is unnecessary to the system of detecting albumin based on the colorimetric assay of the present disclosure. Hence, the present disclosure only applies the image capturing device disposed with the image sensor such as a cell or a mobile device without adding the external apparatuses such as a fluorescent microscope, a mercury lamp, and so on. In addition, by means of replacing the particles of the conventional ion-exchange resin with the circular ion exchange membrane, the present disclosure is capable of showing the same effect for contributing to the observation.

While the means of specific embodiments in present invention has been described by reference drawings, numerous modifications and variations could be made thereto by those skilled in the art without departing from the scope and spirit of the invention set forth in the claims. The modifications and variations should in a range limited by the specification of the present invention.

What is claimed is:

1. A method for detecting albumin based on a colorimetric assay, comprising:
    adding gold nanoparticles into a sample preparing device having a sample without spectroscopic tags, preparing the sample without spectroscopic tags to form an alkaline solution to avoid interference substances adhering on the gold nanoparticles;
    concentrating the gold nanoparticles by using a microfluidic concentrator with a circular ion exchange membrane and by applying an external electric field across two electrodes;
    capturing an image of the concentrated gold nanoparticles by an image capturing device for measuring saturation intensities of the image, wherein there is a relation between the saturation intensities and a concentration of the albumin in the sample without spectroscopic tags; and
    obtaining the concentration of the albumin of the sample without spectroscopic tags by using the relation and the measured saturation intensities.

2. The method for detecting albumin based on the colorimetric assay of claim 1, wherein the saturation intensities comprise a saturation intensity difference among three primary colors of the image.

3. The method for detecting albumin based on the colorimetric assay of claim 2, wherein the relation denotes a linear relation between the saturation intensity difference and a logarithm of the concentration of the albumin.

4. The method for detecting albumin based on the colorimetric assay of claim 1, wherein a pH value of the alkaline solution is substantially 10.

5. The method for detecting albumin based on the colorimetric assay of claim 1, wherein the image capturing device is a charge coupled device or a complementary metal oxide semiconductor image sensor built in a mobile device.

6. A system of detecting albumin based on a colorimetric assay, comprising:
    a sample preparing device having a sample without spectroscopic tags, gold nanoparticles added into the sample preparing device, wherein the sample without spectroscopic tags are prepared to form an alkaline solution to avoid interference substances adhering on the gold nanoparticles when the gold nanoparticles are added into the sample preparing device having the sample without spectroscopic tags;
    a microfluidic concentrator concentrating the gold nanoparticles by using a circular ion exchange membrane and by applying an external electric field across two electrodes;
    an image capturing device capturing an image of the concentrated gold nanoparticles for measuring saturation intensities of the image, wherein there is a relation between the saturation intensities and a concentration of the albumin in the sample without spectroscopic tags; and
    a processing device, the image capturing device transmitting the saturation intensities to the processing device, and the processing device obtaining the concentration of the albumin of the sample without spectroscopic tags by using the relation and the measured saturation intensities.

7. The system of detecting albumin based on the colorimetric assay of claim 6, further comprising a storage storing the relation.

8. The system of detecting albumin based on the colorimetric assay of claim 6, wherein the saturation intensities comprise a saturation intensity difference among three primary colors of the image, and the relation denotes a linear relation between the saturation intensity difference and a logarithm of the concentration of the albumin.

9. The system of detecting albumin based on the colorimetric assay of claim 6, wherein a pH value of the alkaline solution is substantially 10.

10. The system of detecting albumin based on the colorimetric assay of claim 6, wherein the image capturing device is a charge coupled device or a complementary metal oxide semiconductor image sensor built in a mobile device.

* * * * *